(12) United States Patent
Finkelstein

(10) Patent No.: US 10,426,915 B2
(45) Date of Patent: Oct. 1, 2019

(54) SURGICAL INSTRUMENT HAVING AN INTEGRATED LOCAL ANESTHETIC DELIVERY SYSTEM

(71) Applicant: Kenneth Finkelstein, Flossmoor, IL (US)

(72) Inventor: Kenneth Finkelstein, Flossmoor, IL (US)

( * ) Notice: Subject to any disclaimer, the term of this patent is extended or adjusted under 35 U.S.C. 154(b) by 548 days.

(21) Appl. No.: 15/041,244

(22) Filed: Feb. 11, 2016

(65) Prior Publication Data

US 2016/0158484 A1 Jun. 9, 2016

Related U.S. Application Data

(63) Continuation of application No. 12/655,887, filed on Jan. 11, 2010, now Pat. No. 9,277,936.

(51) Int. Cl.
| | |
|---|---|
| *A61M 19/00* | (2006.01) |
| *A61B 17/34* | (2006.01) |
| *A61B 17/3209* | (2006.01) |
| *A61F 2/00* | (2006.01) |
| *A61M 39/22* | (2006.01) |
| *A61B 17/00* | (2006.01) |

(52) U.S. Cl.
CPC ......... *A61M 19/00* (2013.01); *A61B 17/3209* (2013.01); *A61B 17/3478* (2013.01); *A61F 2/0045* (2013.01); *A61M 39/22* (2013.01); *A61B 2017/00805* (2013.01); *A61F 2002/0072* (2013.01)

(58) Field of Classification Search
CPC ...... A61B 2017/00805; A61B 17/3209; A61B 17/3468; A61B 17/3478; A61F 2002/0072; A61M 19/00; A61M 25/0084; A61M 25/0068; A61M 2025/0089; A61M 2025/009; A61M 2025/0091; A61M 5/31526; A61M 5/31581; A61M 5/31586; A61M 5/204; A61M 5/1782; A61M 2005/3114; A61M 2005/3115
See application file for complete search history.

(56) References Cited

U.S. PATENT DOCUMENTS 1,250,965 A * 12/1917 Capwell ............ A61M 5/31581
604/223
2,316,095 A * 4/1943 Mead, Jr. ................ A61M 5/24
604/209

(Continued)

*Primary Examiner* — Kami A Bosworth
(74) *Attorney, Agent, or Firm* — Michael Haynes PLC; Michael N. Haynes

(57) ABSTRACT

A surgical instrument includes a handle portion having a distal end, a proximal end, and a substantially hollow body defining a valve chamber therein; a curved incising tube partially housed within the handle portion adjacent the handle portion proximal end, extending a predetermined distance from the handle portion, and in fluid communication with the valve chamber; a local anesthetic inlet tube partially housed within the handle portion adjacent the handle portion distal end, extending a predetermined distance from the handle portion, and in fluid communication with the valve chamber; a local anesthetic delivery actuator disposed on the handle portion, whereby the local anesthetic delivery actuator is selectively operative between opened and closed valve chamber positions.

26 Claims, 7 Drawing Sheets

(56) References Cited

U.S. PATENT DOCUMENTS

| | | | | |
|---|---|---|---|---|
| 2,632,445 | A * | 3/1953 | Kas, Sr. | A61M 5/31595 188/67 |
| 2,825,334 | A * | 3/1958 | Kas, Sr. | A61M 5/00 222/385 |
| 2,892,457 | A * | 6/1959 | Sturtz | A61M 5/00 222/391 |
| 3,052,240 | A * | 9/1962 | Silver | A61M 5/284 261/69.1 |
| 3,101,711 | A * | 8/1963 | Reitknecht | A61M 5/20 222/390 |
| 3,104,448 | A * | 9/1963 | Morrow | A61M 5/204 141/329 |
| 5,250,065 | A * | 10/1993 | Clement | A61B 17/320016 600/571 |
| 5,454,827 | A * | 10/1995 | Aust | A61B 17/29 600/564 |
| 5,456,672 | A * | 10/1995 | Diederich | A61M 5/31581 433/80 |
| 5,807,340 | A * | 9/1998 | Pokras | A61M 5/204 604/183 |
| 6,200,302 | B1 * | 3/2001 | Johnson | A61M 37/00 604/239 |
| 6,461,296 | B1 * | 10/2002 | Desai | A61B 8/0841 600/210 |
| 2003/0018299 | A1 * | 1/2003 | Stone | A61B 17/0625 604/135 |
| 2009/0137861 | A1 * | 5/2009 | Goldberg | A61B 17/0493 600/30 |
| 2011/0030191 | A1 * | 2/2011 | Weill | A61M 5/1782 29/428 |

* cited by examiner

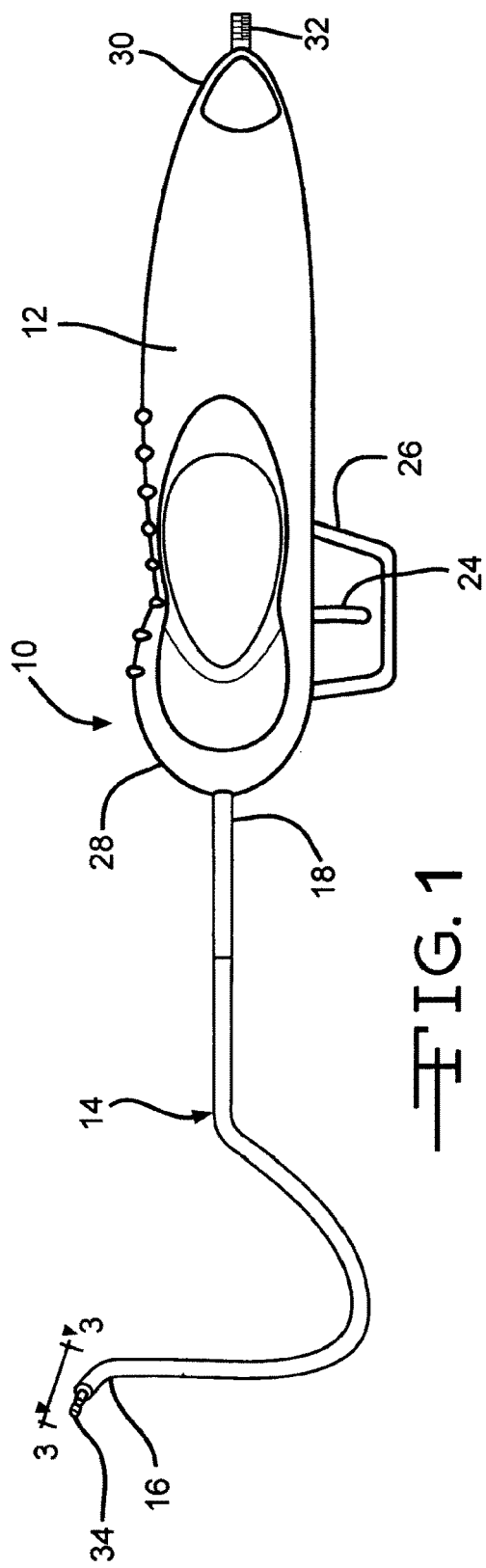
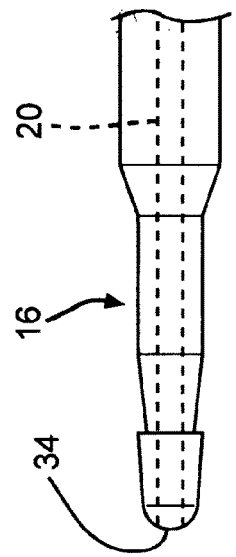
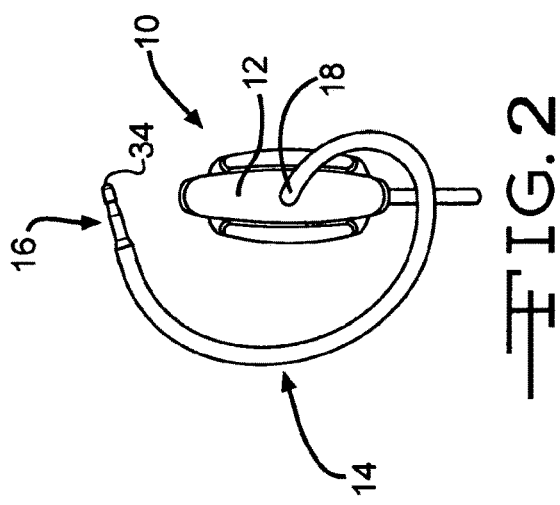
FIG. 1
FIG. 3
FIG. 2

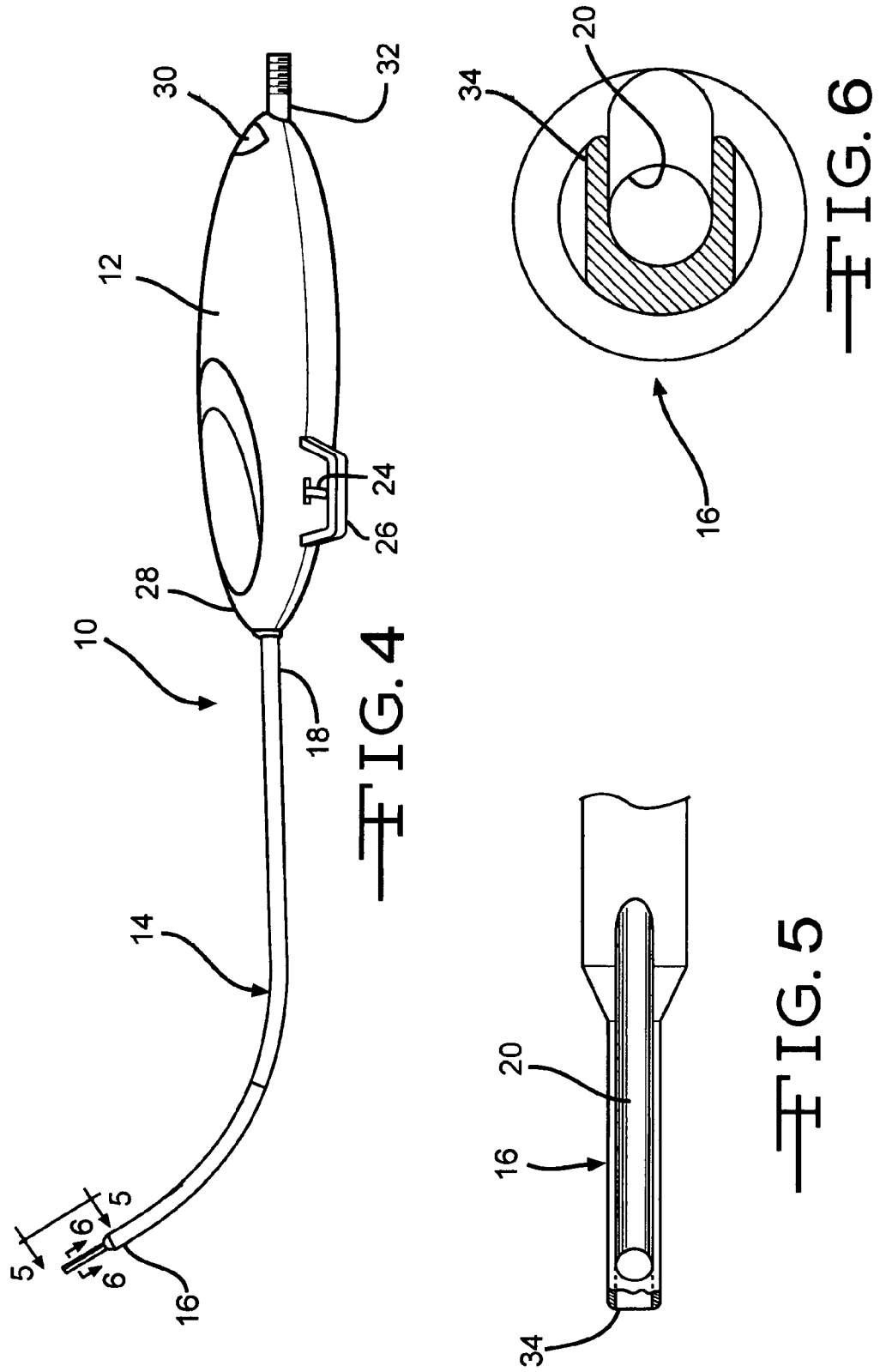

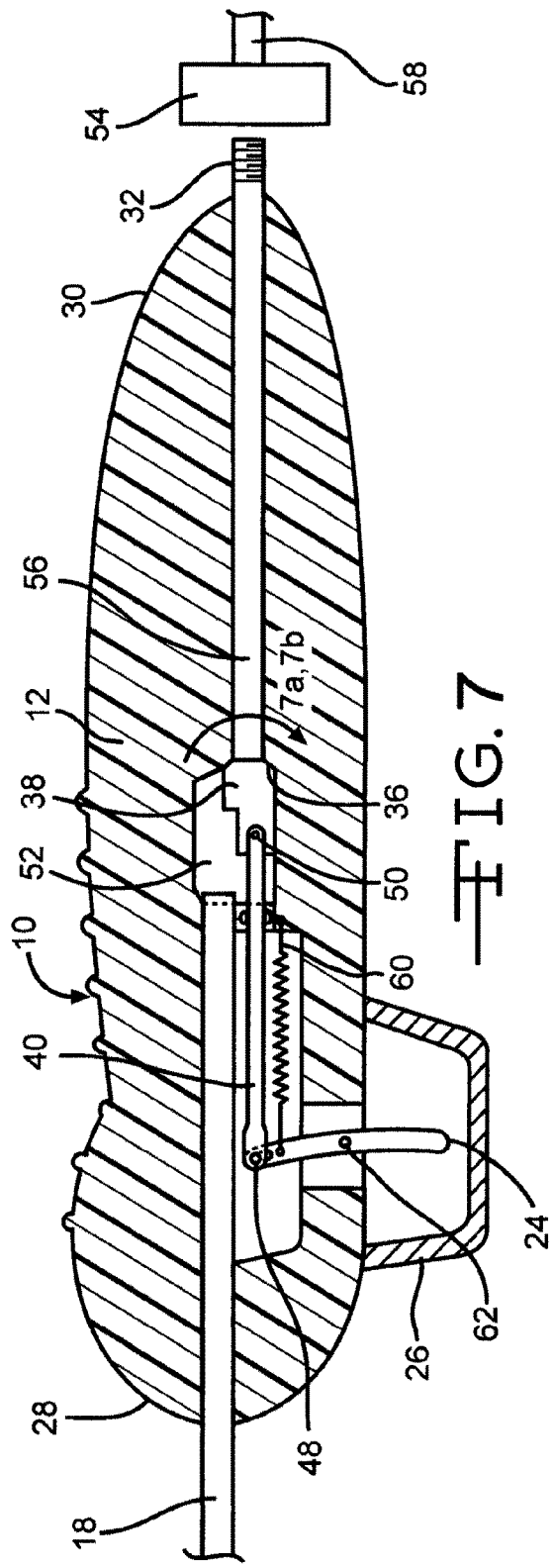
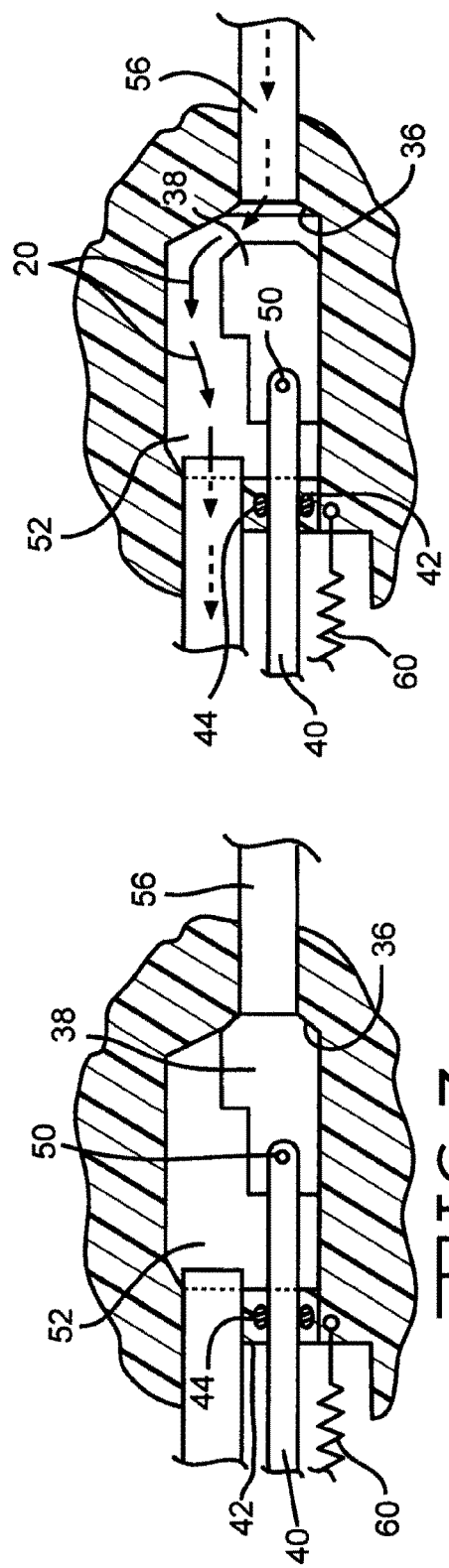

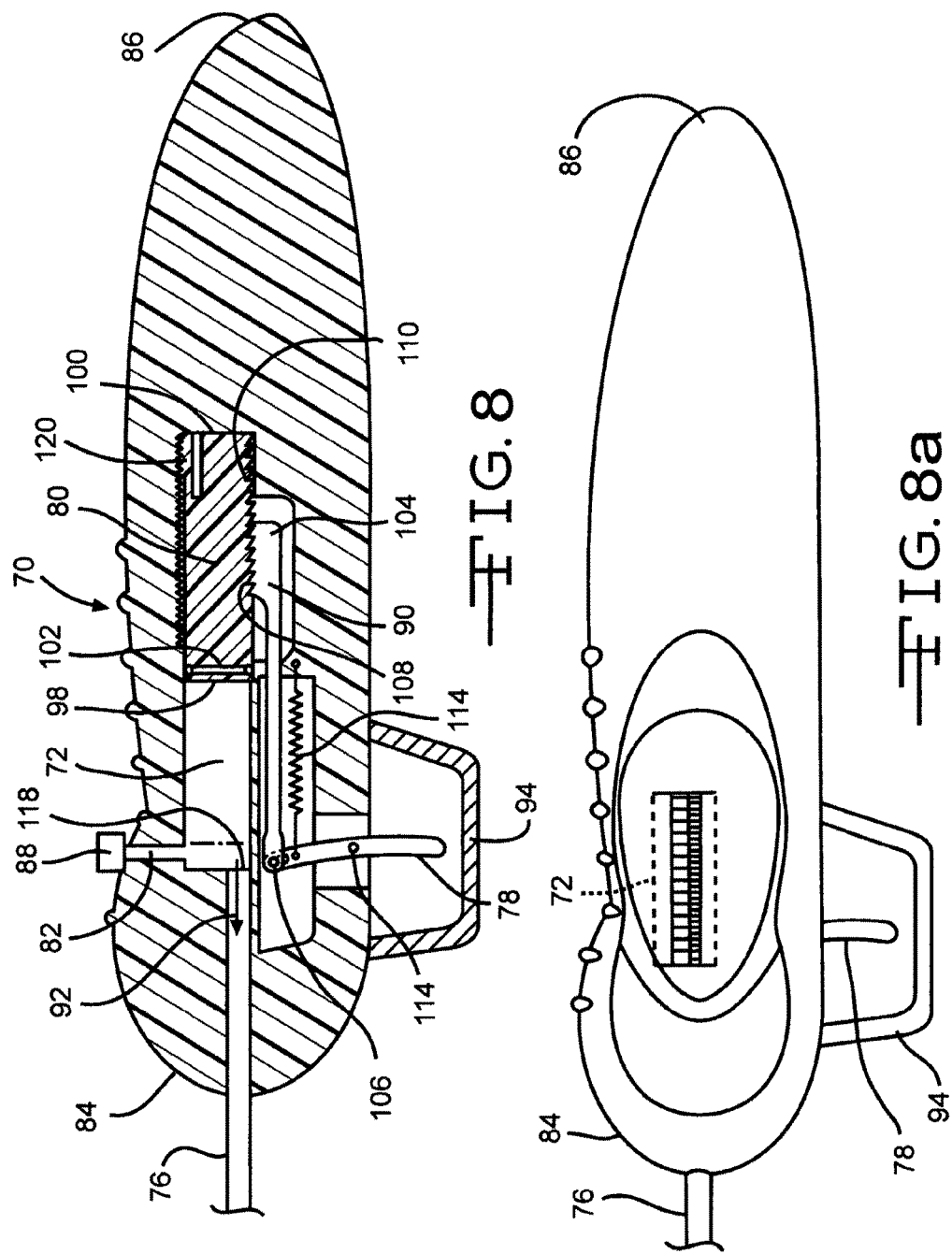

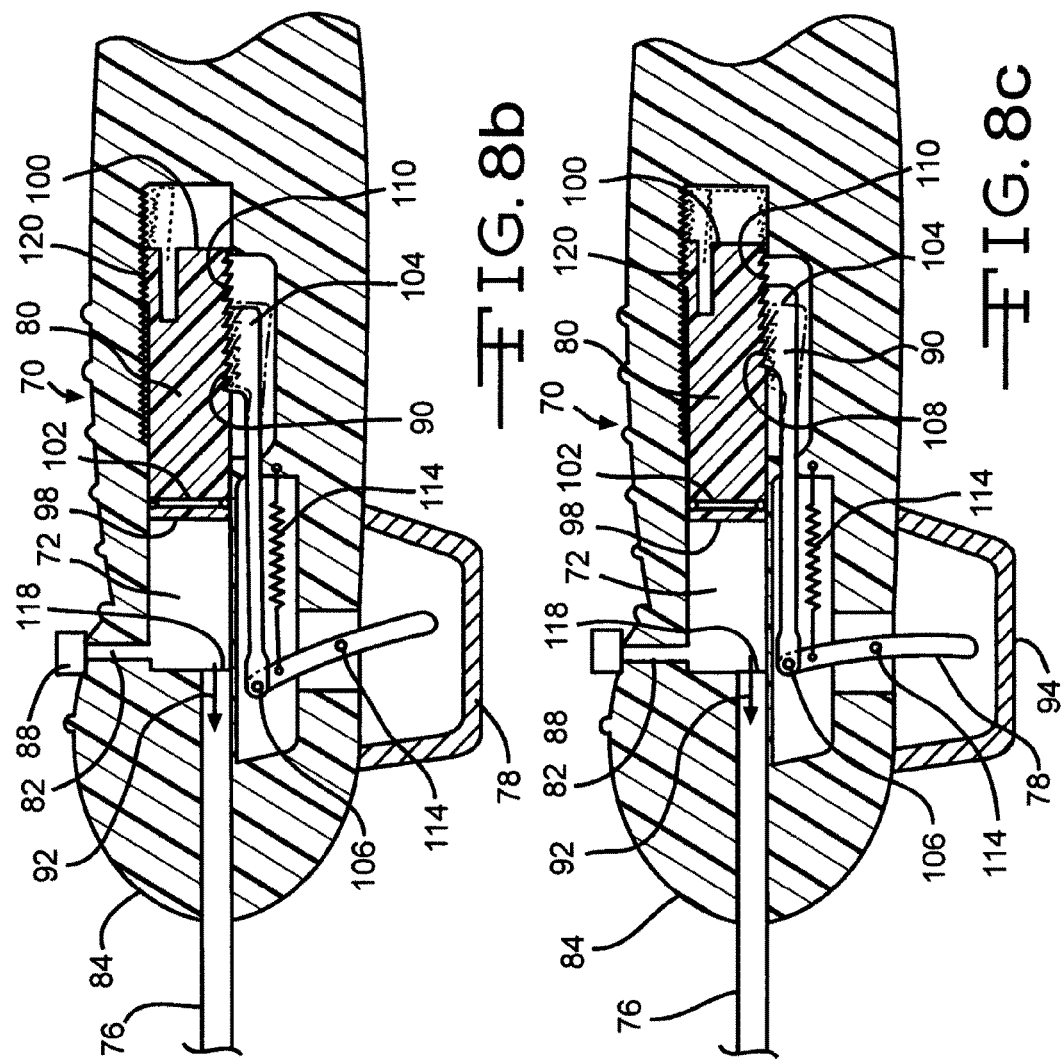

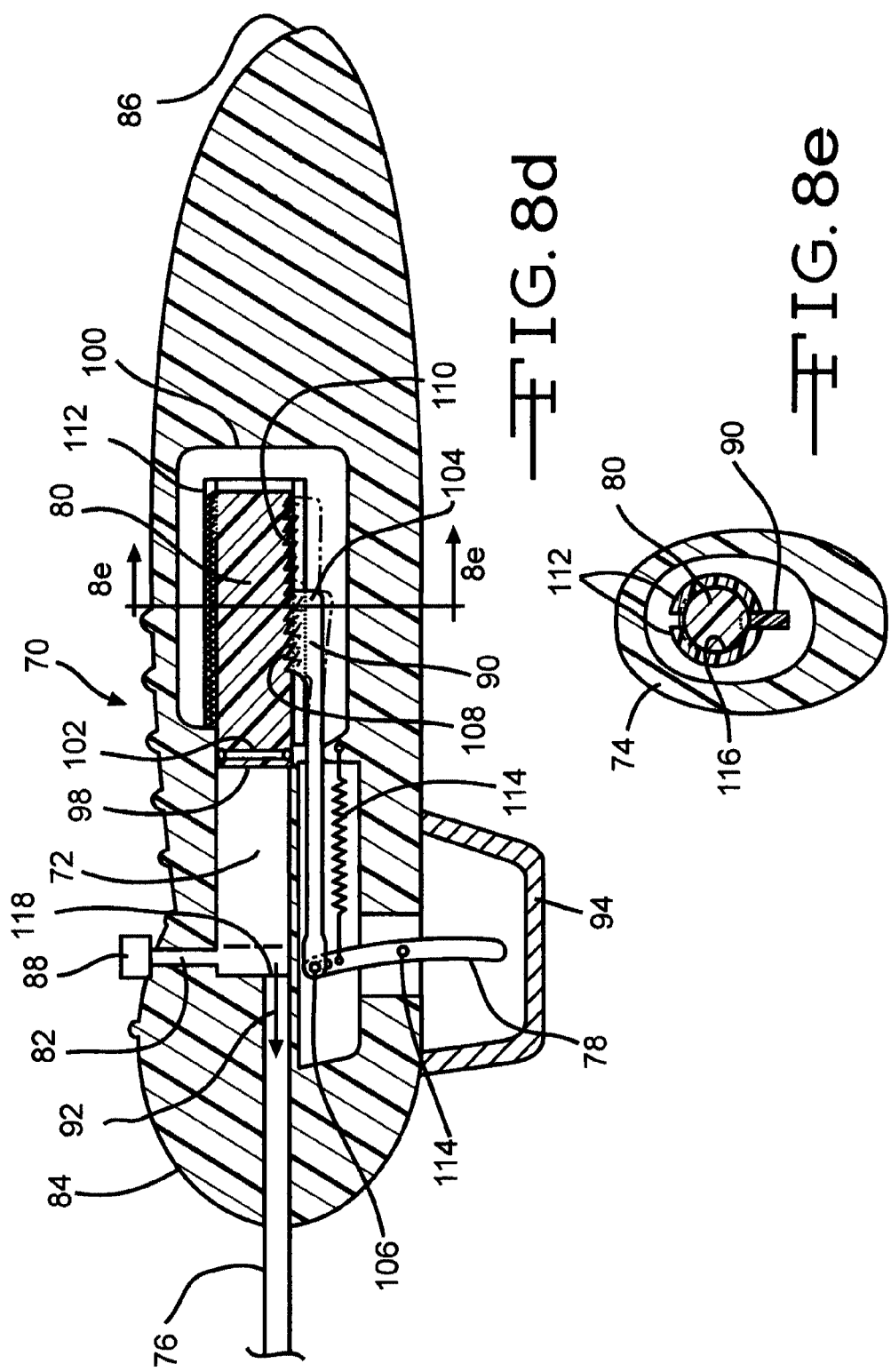

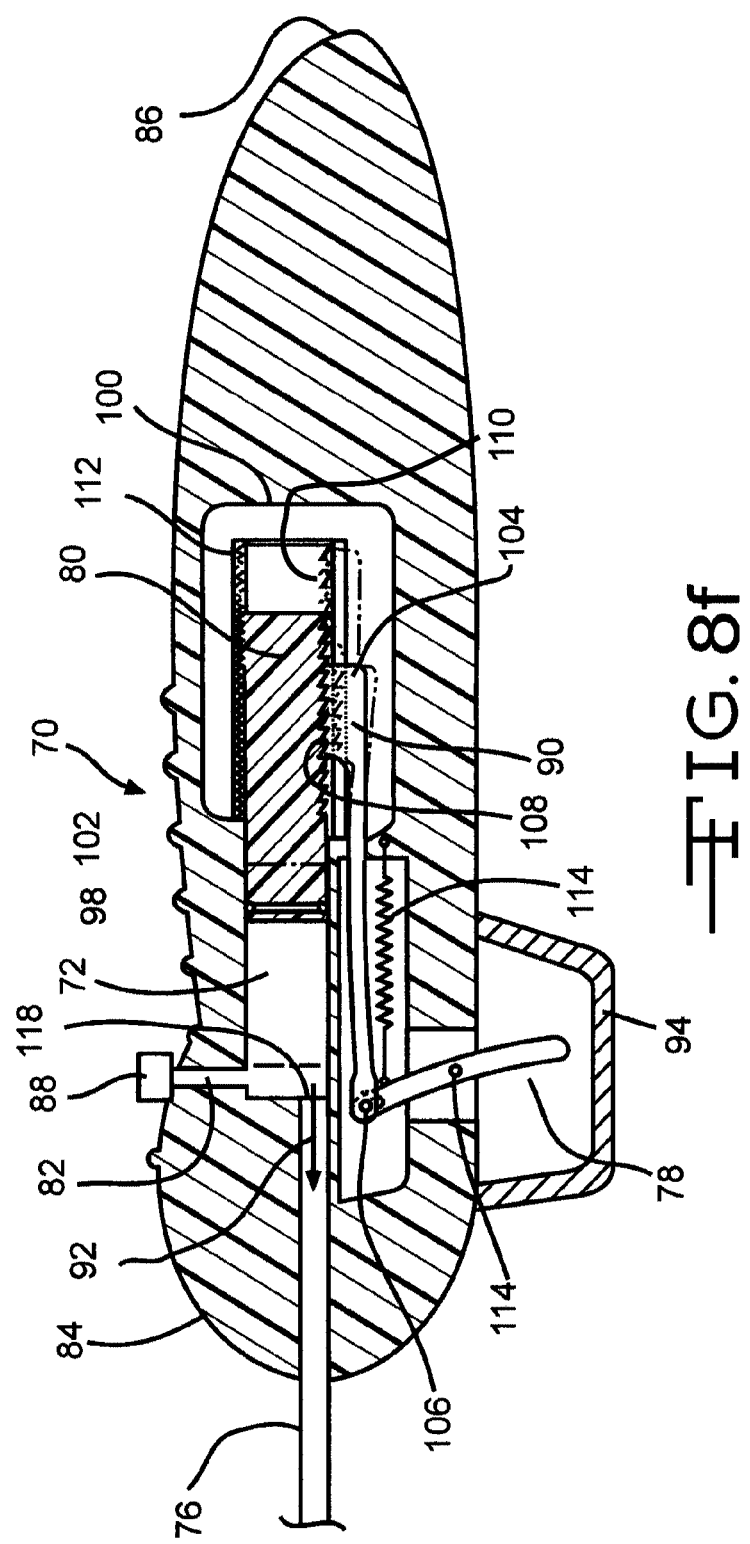

SURGICAL INSTRUMENT HAVING AN INTEGRATED LOCAL ANESTHETIC DELIVERY SYSTEM

FIELD

Certain exemplary embodiments relate to a surgical instrument, and more specifically, a surgical instrument used in surgery for treatment of female urinary incontinence having an integrated local anesthetic delivery system.

BACKGROUND

Women account for over 10 million of the diagnosed incontinence cases. A majority of women dealing with incontinence suffer from stress urinary incontinence ("SUI"). Generally, women with SUI involuntarily lose urine during normal daily activities, such as laughing, coughing, and regular exercise.

Specifically, SUI is commonly caused by a functional defect of the tissue or ligaments connecting the vaginal wall with the pelvic muscles and pubic bone. Typical causes include repetitive straining of the pelvic muscles, childbirth, loss of pelvic muscle tone, and estrogen loss. These types of defects result in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle, shying away from social situations.

Non-operative treatment options for patients with SUI can be attempted, by instructing such patients to perform pelvic exercises, known as "Kegel" exercises, with the intention of strengthening the supporting muscles. However, when these exercises fail to reverse SUI, surgical repair is advised.

Among the many surgical options for SUI, the introduction into the abdominal cavity of a urethral "sling" has emerged in the past decade as the most effective. In this surgical procedure, the sling, typically in the form of a mesh or tape-like material, shaped like a flat ribbon, is passed through pelvic tissue and is positioned around the urethra and the bladder neck, forming a loop located between the urethra and the vaginal wall and thereby creating a supportive sling effect. The sling is extended over the pubis and through the abdominal wall and is tightened, after which the surplus material is cut and removed, and the sling is left implanted in the patient's abdominal cavity.

U.S. Pat. No. 5,899,909 discloses a treatment method and device for SUI. The device described, which allows a mesh or tape-like sling to be placed under the urethra, and includes two special needles. These are mounted in turn, by screw fastening, on a reusable steel insertion tool made of a handle and of a threaded manipulator rod, which allows each of the needles to be manipulated in turn. Each needle is fixed to one of the ends of the sling.

Often patients needing the surgical sling procedure are uncomfortable general anesthetic and would prefer the procedure be performed as an outpatient surgery with local anesthetic. It would therefore be beneficial to provide a surgical instrument for use in treating SUI that has a local anesthetic delivery system integrated therein. It would also be beneficial to provide a surgical instrument for use in treating SUI that allows the instrument operator to administer the local anesthetic with one hand, as it is often the case that a second hand is needed to guide the incising portion of the surgical instrument through the patient's abdominal fascia and soft tissue.

Each of certain exemplary embodiments addresses that need and advantageously overcomes the deficiencies of the prior art.

SUMMARY

Certain exemplary embodiments can provide a surgical instrument having an integrated local anesthetic delivery system that overcomes the disadvantages of the prior art.

Accordingly, certain exemplary embodiments can advantageously provide a surgical instrument that includes a handle portion having a distal end, a proximal end, and a substantially hollow body defining a valve chamber therein. The surgical instrument also includes a curved incising tube partially housed within the handle portion adjacent the handle portion proximal end, extending a predetermined distance from the handle portion, terminating at an incising tip, and in fluid communication with the valve chamber. The surgical instrument further includes a local anesthetic inlet tube partially housed within the handle portion adjacent the handle portion distal end, extending a predetermined distance from the handle portion, terminating at an inlet port, and in fluid communication with the valve chamber.

It is a feature of certain exemplary embodiments that the surgical instrument includes a local anesthetic delivery actuator disposed on the handle portion, whereby the local anesthetic delivery actuator is selectively operative between opened and closed valve chamber positions.

BRIEF DESCRIPTION OF THE DRAWINGS

These and other objects, advantages, and features of certain exemplary embodiments will become apparent from a reading of the following detailed description with reference to the accompanying drawings, in which:

FIG. 1 is a perspective view of a surgical instrument;

FIG. 2 is a side view of a surgical instrument;

FIG. 3 is a partial view of a surgical instrument;

FIG. 4 is a perspective view of an alternative embodiment of a surgical instrument;

FIG. 5 is a partial view of an alternative embodiment of a surgical instrument;

FIG. 6 is a partial view of an alternative embodiment of a surgical instrument;

FIG. 7 is a cut-away view of a handle portion for a surgical instrument;

FIG. 7a is a partial cut-away view of FIG. 7 of a handle portion for a surgical instrument;

FIG. 7b is a partial cut-away view of FIG. 7 of a handle portion for a surgical instrument;

FIG. 8 is a partial cut-away view of an alternative embodiment of a handle portion for a surgical instrument;

FIG. 8a is a partial side view of an alternative embodiment of a handle portion for a surgical instrument;

FIG. 8b is a partial cut-away view of an alternative embodiment of a handle portion for a surgical instrument;

FIG. 8c is a partial cut-away view of an alternative embodiment of a handle portion for a surgical instrument;

FIG. 8d is a partial cut-away view of an alternative embodiment of a handle portion for a surgical instrument;

FIG. 8e is a cross-sectional view along the line 8e-8e of FIG. 8d; and

FIG. 8f is a partial cut-away view of an alternative embodiment of a handle portion for a surgical instrument;

DESCRIPTION OF THE PREFERRED EMBODIMENT(S)

Certain exemplary embodiments comprise an apparatus and surgical instrument 10 used in a surgical procedure for the treatment of SUI. Generally, the surgical instrument 10 is used to incise a path in the lower abdomen of a patient and insert a mesh or tape sling (not shown), through pelvic fascia and soft tissue, which is positioned between the urethra and vaginal wall. The sling offers support to the tissue of the lower abdomen, especially to the patient's urethra, and helps prevent urinary incontinence, as is known in the art. Specifically, when pressure is exerted upon the lower abdomen, such as during a cough or sneeze, the sling provides support to the urethra, allowing it to keep its seal and prevent an unwanted discharge of urine.

Referring to FIGS. 1-7, certain exemplary embodiments generally comprise a surgical instrument 10 that is advantageously adapted to administer a local anesthetic to a patient during surgery. The application of a predetermined local anesthetic to a patient from a pressurized remote reservoir (not shown) is facilitated via a local anesthetic delivery passageway 20 extending through said surgical instrument 10. Suitable local anesthetics are generally known in the art.

Referring to FIGS. 1, 4, and 7, a surgical instrument 10 includes: a handle portion 12 having a substantially hollow body, housing a valve mechanism (described in greater detail below) having a local anesthetic delivery actuator 24; a curved incising tube partially housed by said handle portion 12; and a local anesthetic inlet tube 56, also partially housed by said handle portion. The handle portion 12 has a distal end 28, a proximal end 30, and a substantially hollow body extending therebetween; a portion of which defines a valve chamber 52. The handle portion 12 may be made of multiple suitable materials, such as a polymeric based material and steel or other suitable metal, as is known in the art. The curved incising tube 14 is partially housed within the handle portion 12 adjacent the handle portion distal end 28, and extends a predetermined distance from said handle portion distal end 28, terminating at an incising tip 34. The local anesthetic inlet tube 56 is partially housed within the handle portion 12 adjacent the handle portion proximal end 30, and extends a predetermined distance from said handle portion proximal end 30, terminating at an inlet port 32. The valve mechanism is housed within the handle portion 12 and is manipulated by the local anesthetic delivery actuator 24, which is pivotally attached to said handle portion 12.

The local anesthetic delivery actuator 24 operates the valve mechanism and valve chamber 52 between closed and opened valve chamber positions, as shown in FIGS. 7a and 7b respectively. Advantageously, the local anesthetic delivery actuator 24 allows a surgeon to selectively administer local anesthetic by manipulating the valve mechanism with a single hand. When the valve mechanism is manipulated to the open position by the surgeon the incising tube 14, handle portion 12, and local anesthetic inlet tube 56 are in fluid communication and define a local anesthetic delivery passageway 20.

The curved incising tube 14 has a proximal end 18, a distal end 16, and a hollow, preferably cylindrical, body extending therebetween. The incising tube distal end 16 terminates at an incising tip 34, and preferably has a substantially circular cross-section. Advantageously, the incising tip 34 of the incising tube 14 is rounded (see FIG. 3) or blunt (see FIG. 5), wherein the conical tip may have a radius of approximately 0.5 millimeters. A blunt tip is preferred since it is less likely to stick in bone or penetrate bladder wall tissue or blood vessel wall tissue. The incising tube proximal end 18 is partially housed within the handle portion 12 and extends a predetermined distance inward adjacent the handle portion distal end 28. The incising tube proximal end 18 extends to the valve chamber 52 within the handle portion 12. The entire length of the incising tube 14 is hollow and in fluid communication with said valve chamber 52. The incising tube 14 may be helical or planar in curvature, as shown in FIGS. 1 and 4 respectively. The incising tube 14 is preferably made from a material that is compatible with the human body. For example, the incising tube 14 may be made from AISI 303 stainless steel. The surface of the incising tube 14 is preferably smooth and polished, to facilitate penetration of a patient's fascia and soft tissue.

As best shown in FIG. 7, the local anesthetic inlet tube 56 is also partially housed within the handle portion 12, has a hollow body, and a local anesthetic inlet port 32 that extends a predetermined distance from the handle portion proximal end 30. The local anesthetic inlet port 32 is preferably threaded to facilitate coupling to a local anesthetic delivery tube 58 with a Lever-Lock or Luer-Lock type fastener 54, or other suitable fastener as are known in the art. At the opposite end of the inlet port 32, the local anesthetic inlet tube 56 extends to the valve chamber 52 within the handle portion 12. The entire length of the local anesthetic inlet tube 56 is in fluid communication with said valve chamber 52. Preferably, the local anesthetic inlet tube 56 is cylindrical, with a circular cross section, and is made from AISI 303 stainless steel.

As shown in FIG. 7, the handle portion 12 advantageously houses a valve mechanism that is manipulated by a local anesthetic delivery actuator 24, which is pivotally attached to said handle portion 12. The local anesthetic delivery actuator 24 allows a surgeon to selectively activate the valve mechanism and valve chamber 52 between open and closed positions, described in greater detail below. When the valve mechanism is in the open position the incising tube 14, valve chamber 52, and local anesthetic inlet tube 56 define the local anesthetic delivery passageway 20 for the application of local anesthetic to the patient.

As further shown in FIG. 7, the local anesthetic delivery mechanism is disposed within the handle portion 12, in fluid communicating relationship and intermediate the local anesthetic inlet tube 56 and the incising tube 14. The local anesthetic inlet tube 56 and the incising tube 14 are preferably disposed in parallel but axially offset relation to the valve chamber 52. The valve chamber 52 intersects and separates the local anesthetic deliver tube 56 from the incising tube 14, while offering selectively operable flow of local anesthetic. The local anesthetic delivery actuator 24 preferably has an actuator guard 26 in order to prevent inadvertent application of the local anesthetic.

More specifically with respect to FIGS. 7, 7a, and 7b, the local anesthetic delivery mechanism includes, a valve seat 36 at one end of the chamber that is shaped to receive a valve member 38 in sealing engagement therewith. The valve member 38 is mounted on one end of an elongated valve stem 40 and is designed to reciprocate within the valve chamber 52 between an opened position, as shown in FIG. 7b, and a closed position abutting the valve seat 36, as shown in FIG. 7a. The valve stem 40 is coupled to the valve member 38 by a pin 50 at one end, and to the local anesthetic delivery actuator 24, via a pivot pin 48, at an opposing end. The local anesthetic delivery actuator 24 is pivotally mounted 62 to the handle portion 12 and is biased to the closed position, as shown in FIG. 7a, by preferably a contractile spring type biasing member 60. A tubular bearing sleeve 42 is mounted in the valve chamber 52 and carries an annular sealing ring 44 within a groove of the bearing sleeve 42. The valve stem 40 projects through an axial bore in the bearing sleeve 42 and is arranged to reciprocate in the bearing sleeve 42 in response to manual operation of the local anesthetic delivery actuator 24. Reciprocation of the valve stem 40 is obtained by manually squeezing the local anesthetic delivery actuator 24.

The surgical procedure for trans-abdominally implanting mesh (not shown) with a surgical instrument 10 under general anesthesia is known in the art. Typically, the relevant parts of a female patient's lower abdomen involved are, the vagina, the uterus, the urethra, the pubic bone, the urinary bladder, and the abdominal wall. A surgeon uses the instrument to enter the vagina and implanting the ends of a mesh into endopelvic fascia and/or muscle with the mesh placed at the mid-urethra vicinity or by placing the incising tube through the skin and the obturater space into the vagina to deliver the mesh to the vicinity of the mid-urethra or conversely from the vagina out through the obturator space.

Each of certain exemplary embodiments advantageously improves the above method by providing for local anesthetic to be administered at various positions along the aforesaid pathway through the patient's abdomen, thereby foregoing the need for general anesthesia and an overnight stay in a hospital for the patient. As the incising tube 14 moves through the patient's abdomen, the patient communicates with the surgeon as to the level of discomfort, whereby the incising tube 14 is paused, the local anesthetic delivery actuator 24 is manipulated to the open position (see FIG. 7b), and a clinically effective amount of local anesthetic is administered to the patient before moving the incising tube 14 further along. This process is repeated throughout surgery as needed. The incising tube 14 may be paused and local anesthetic injected as many times as the surgeon deems necessary, depending upon the condition of the patient and other clinical factors, with which persons having ordinary skill in the art will be familiar. Advantageously, this procedure may be performed using local anesthesia, rather than general anesthesia, and can be performed as an outpatient procedure in the surgeon's office or another outpatient facility, rather than requiring admission to a hospital. Additionally, the patient is able to provide feedback to the surgeon during the procedure.

Referring to FIGS. 8-8f, alternative embodiments generally comprise a surgical instrument 70 that is adapted to administer a local anesthetic to a patient during surgery, which advantageously utilizes an internally integrated pressurization mechanism for delivering such anesthetic. The application of a predetermined local anesthetic to a patient from an internally pressurized mechanism is facilitated via an internal local anesthetic reservoir 72 disposed within a handle portion 74 being in fluid communication with an incising tube 76, wherein the anesthetic is selectively administered via an actuator 78 in ratcheting engagement with a plunger 80, which is partially housed within the reservoir 72. Suitable local anesthetics are generally known in the art.

More specifically, with respect to FIGS. 8d and 8f, the surgical instrument 70 includes: a handle portion having a substantially hollow body, housing an internally integrated pressurization mechanism for delivering local anesthetic (described in greater detail below), the handle portion 74 having a local anesthetic delivery actuator 78; a curved incising tube 76 partially housed by said handle portion 74; and a local anesthetic fill tube 82, also partially housed by said handle portion 74. The handle portion 74 has a distal end 84, a proximal end 86, and a substantially hollow body extending therebetween; a portion of which defines a preferably cylindrical local anesthetic reservoir 72. The handle portion 74 may be made of multiple suitable materials, such as a polymeric based material, as is known in the art. The curved incising tube 76 is partially housed within the handle portion 74 adjacent the handle portion distal end 84, and extends a predetermined distance from said handle portion distal end 84, preferably terminating at an incising tip as described above in the previous embodiment. The local anesthetic fill tube 82 is partially housed within the handle portion 74 adjacent the handle portion distal end 84, and extends a predetermined distance from said handle portion 74, terminating at a pressure release type valve cap 88. Any suitable valve cap, as are known in the arts, may accomplish the function of pressure release without fluid release, such as a radiator cap used in the automotive arts. The internally integrated pressurization mechanism is housed within the handle portion 74 and is manipulated by the local anesthetic delivery actuator 78, which is pivotally attached to the handle portion 74.

The local anesthetic delivery actuator 78 operates a ratcheting mechanism between ratchet and return positions, as shown in FIGS. 8f and 8d respectively. Advantageously, the local anesthetic delivery actuator 78 allows a surgeon to selectively administer local anesthetic, by manipulating an elongated ratcheting stem 90 slidingly coupled to a ratcheting type plunger 80, with a single hand and without needing an external pressurization system as disclosed in the above embodiment. When the internally integrated pressurization mechanism is manipulated to the ratcheted position by a surgeon, local anesthetic is forced out of the local anesthetic reservoir 72, through the incising tube 76, and out the incising tube tip. The local anesthetic fill tube 82, local anesthetic reservoir 72, and incising tube 76 are in fluid communication and define a local anesthetic delivery passageway 92.

As best shown in FIG. 8d, the local anesthetic fill tube 82 is partially housed within the handle portion 74, has a hollow body, and extends a predetermined distance from the handle portion distal end 84. The local anesthetic fill tube 82 is operative between fill and capped functions via a pressure release valve cap 88. The local anesthetic fill tube 82 extends from the valve cap 88 to the local anesthetic reservoir within the handle portion 74, being in fluid communication with the reservoir 72 and incising tube 76. Preferably, the local anesthetic fill tube 82 is cylindrical, with a circular cross section, and is made from AISI 303 stainless steel.

As shown in FIGS. 8d and 8f, the handle portion advantageously houses an internally integrated pressurization mechanism that is manipulated by a local anesthetic delivery actuator 78, which is pivotally attached to said handle portion 74. The local anesthetic delivery actuator 78 allows a surgeon to selectively activate the pressurization mechanism and urge incremental doses of local anesthetic out of the reservoir 72 and into the incising tube 76 through to a patient.

Advantageously, as further shown in FIGS. 8d and 8f, the local anesthetic delivery mechanism is disposed within the handle portion 74. The reservoir 72 intersects and separates the local anesthetic fill tube from the incising tube 76. The local anesthetic delivery actuator 78 preferably has an actuator guard 94 in order to prevent inadvertent application of the local anesthetic. The handle portion further advantageously includes a measured dosing window 96, see FIG. 8a, disposed adjacent the reservoir 72, which allows the surgeon to measure how much local anesthetic is being delivered to the patient during surgery. The increments may be in any accepted volume time measurement designations, whether English or Metric systems.

More specifically with respect to FIGS. 8d and 8f, the integrated pressurization mechanism includes, a plunger 80 at one end of the reservoir 72 having the same preferably cylindrical cross-section as the reservoir 72. The plunger 80 has a distal plunger end 98 partially disposed within the reservoir 72 and adapted to unidirectionally move through the reservoir 72 upon operation of the actuator 78. The plunger 80 carries an annular sealing ring 102 within a groove of the plunger 80 adjacent the plunger distal end 98. The plunger 80 further has a ratcheting end 100 opposite the distal end 98. The ratcheting end 100 of the plunger 80 has a plurality of ratcheting teeth or keys 110. The ratcheting stem 90 projects through an axial bore 104 in the handle and is arranged to reciprocate in the handle axial bore 104 in response to manual operation of the local anesthetic delivery actuator 78. The ratcheting stem 90 is slidingly coupled to the plunger 80 with unidirectionally angled teeth or serrated keys 108 disposed on one end of the stem 90, and to the local anesthetic delivery actuator 78 via a pivot pin 106 at an opposing end. As the ratcheting stem 90 moves in response to operation by a surgeon manually engaging the actuator 78, see FIG. 8f, the serrated keys 108 engage correspondingly angled keys 110 of plunger 80 adjacent the ratcheting end 100 thereof. The local anesthetic delivery actuator 78 is pivotally mounted 114 to the handle portion 74 and is biased to the return position, as also shown in FIG. 8d, by a contractile spring type biasing member 114. As shown in FIG. 8d, as the actuator moves to the return position via the biasing member 114, the unidirectionlly angled teeth 108 of the stem 90 slide over the plunger keys 110 and the stem 90 deflects away from the plunger 80 incrementally. A pair of semi-cylindrical opposing locking fingers 112 are disposed adjacent the ratcheting end 100 of the plunger 80, each finger 112 has a plurality of locking teeth 116 disposed in contacting relationship with the plunger ratcheting keys 110. As the plunger 80 is urged through the reservoir 72 in progressive increments (visually discernable through the dosing window 96) via manual operation of the actuator 78, the locking fingers 112 flex outward to accommodate such movement. When the actuator 78 is released and the stem 90 is biased back to the return position, the locking fingers 112 return to contacting relation with the locking teeth 116 of the plunger 80, wherein the teeth 116 of the fingers 112 engage the ratcheting keys 110 of the plunger 80 thereby holding the plunger 80 in place. A still further embodiment of a ratcheting mechanism is shown in FIGS. 8, 8b, and 8c, for the present application wherein the plunger 80 has a flexible ratcheting finger 120 that deflects as the plunger 80 is urged into the reservoir 72 and returns to engage locking teeth 110 in handle 74.

The above and other ratcheting mechanisms may serve the function of incrementally urging the plunger 80 through the reservoir 72 without departing from the scope of the present application. Such ratcheting arrangement being such that linear translation of the ratcheting stem 90 between ratchet and return positions, via the actuator 78, is translated into unidirectional linear motion of the plunger 80 into the reservoir 72; thereby affecting pressurization of the reservoir 72 in order to facilitate passage of the local anesthetic out of the reservoir 72 and through and out of the incising tube 76 to the patient. Should pressurization of the reservoir 72 reach a state where manual operation of the actuator 78 is overly cumbersome, the valve cap 88 may be actuated to affect release of such pressure.

The surgical procedure for trans-abdominally implanting mesh (not shown) with a surgical instrument 70 under general anesthesia is known in the art. Typically, the relevant parts of a female patient's lower abdomen involved are, the vagina, the uterus, the urethra, the pubic bone, the urinary bladder, and the abdominal wall. A surgeon uses the instrument to enter the vagina and implanting the ends of a mesh into endopelvic fascia and/or muscle with the mesh placed at the mid-urethra vicinity or by placing the incising tube through the skin and the obturater space into the vagina to deliver the mesh to the vicinity of the mid-urethra or conversely from the vagina out through the obturator space. The surgeon then repeats the same procedure, but passing the incising tube 76 on the opposite side of the urethra, to complete the implantation of the mesh between the mid-urethra and vaginal wall.

Each of certain exemplary embodiments advantageously improves the above method by providing for local anesthetic to be administered at various positions along the aforesaid pathway through the patient's abdomen without having to couple the surgical instrument to an external local anesthetic source, also thereby foregoing the need for general anesthesia and an overnight stay in a hospital for the patient. Specifically, the valve cap 88 is removed and a predetermined amount and type of local anesthesia is placed into the reservoir 72 via the fill tube 82. Once the valve cap 88 is replaced the surgeon may begin operating. As the incising tube 76 moves through the patient's abdomen, the patient communicates with the surgeon as to the level of discomfort, whereby the incising tube 76 is paused, the local anesthetic delivery actuator 78 is manipulated to the ratchet position (see FIGS. 8b and 8f), and a clinically effective amount of local anesthetic is administered to the patient, by internally pressurizing the reservoir, before moving the incising tube 76 further along. This process is repeated throughout surgery as needed. The incising tube 76 may be paused and local anesthetic injected as many times as the surgeon deems necessary, depending upon the condition of the patient and other clinical factors, with which persons having ordinary skill in the art will be familiar. Advantageously, this procedure may be performed using local anesthesia, rather than general anesthesia, does not need an externally pressurized source of local anesthetic as needed for the first embodiment, and can be performed as an outpatient procedure in the surgeon's office or another outpatient facility, rather than requiring admission to a hospital.

While a multiple embodiments have been illustrated and described in detail, it should be understood that various modifications in design and details of construction are possible without departing from the spirit of this invention or the scope of the following claims.

What is claimed is:

1. A surgical instrument configured for locally delivering anesthetic while implanting a mechanism configured for treating female urinary incontinence, the surgical instrument comprising:
   a handle portion defining a reservoir;
   a longitudinally curved sling- and anesthetic-delivery incising tube in fluid communication with the reservoir, and configured to:
      form a path in the abdomen of the patient;
      move a sling through pelvic fascia of the patient; and position the sling between the patient's urethra and vaginal wall;

an anesthetic delivery actuator that is connected to a biasing member, in ratcheting engagement with a plunger disposed within the reservoir and configured to move the anesthetic delivery actuator; an actuator guard disposed on the handle portion and configured to prevent inadvertent actuation of the anesthetic delivery actuator;

the biasing member;

the plunger; a local anesthetic inlet tube that is partially housed within the handle portion, terminates at an inlet port sealed by a valve cap that provides pressure release without fluid release, and is in fluid communication with the reservoir; and the valve cap;

wherein:
the surgical instrument is configured to locally deliver the anesthetic while assisting the surgeon with forming the path through, moving the sling within, and implanting the sling in, the patient's abdomen.

2. The surgical instrument of claim 1, wherein the anesthetic delivery actuator is selectively operative.

3. The surgical instrument of claim 2, wherein the anesthetic delivery actuator is pivotally disposed on the handle portion.

4. The surgical instrument of claim 1, wherein the longitudinally curved sling- and anesthetic-delivery incising tube terminates at an incising tip.

5. The surgical instrument of claim 1, wherein the inlet port is located a predetermined distance from a distal end of the handle portion.

6. The surgical instrument of claim 1, wherein the handle portion is formed from a polymeric material.

7. The surgical instrument of claim 1, wherein the longitudinally curved sling- and anesthetic-delivery incising tube is formed from a stainless steel material.

8. The surgical instrument of claim 1, wherein the local anesthetic inlet tube is formed from a stainless steel material.

9. A surgical instrument configured for locally delivering anesthetic while implanting a mechanism configured for treating female urinary incontinence, the surgical instrument comprising:

a handle portion defining a reservoir therein;

a longitudinally curved sling- and anesthetic-delivery incising tube in fluid communication with the reservoir, and configured to:
form a path in the lower abdomen of a patient;
move a sling through pelvic fascia of the patient; and
position the sling between the patient's urethra and vaginal wall;

a local anesthetic inlet tube that is partially housed within the handle portion, terminates at an inlet port sealed by a valve cap that provides pressure release without fluid release, and is in fluid communication with the reservoir;

the valve cap;

a local anesthetic delivery actuator connected to a biasing member configured to move the local anesthetic delivery actuator; and an actuator guard;

wherein:
the surgical instrument is configured to locally deliver the anesthetic while assisting the surgeon with forming the path through, moving the sling within, and implanting the sling in, the patient's abdomen.

10. The surgical instrument of claim 9, wherein the longitudinally curved sling- and anesthetic-delivery incising tube terminates at an incising tip.

11. The surgical instrument of claim 9, wherein the inlet port is located a predetermined distance from a distal end of the handle portion.

12. The surgical instrument of claim 9, wherein the local anesthetic delivery actuator is pivotally disposed on the handle portion.

13. The surgical instrument of claim 9, wherein the handle portion is formed from a polymeric material.

14. The surgical instrument of claim 9, wherein the longitudinally curved sling- and anesthetic-delivery incising tube is formed from a stainless steel material.

15. The surgical instrument of claim 9, wherein the local anesthetic inlet tube is formed from a stainless steel material.

16. A surgical instrument, comprising: a
handle portion having a distal end, a proximal end, and a substantially hollow body defining a reservoir therein;

a longitudinally curved incising tube partially housed within the handle portion adjacent the handle portion distal end, extending a predetermined distance from said handle portion terminating at an incising tip, and in fluid communication with said reservoir;

a local anesthetic inlet tube partially housed within the handle portion adjacent the handle portion distal end, extending a predetermined distance from said handle portion terminating at an inlet port sealed by a valve cap that provides pressure release without fluid release, and in fluid communication with said reservoir;

the valve cap; and a local anesthetic delivery actuator disposed on said handle portion;

wherein said local anesthetic delivery actuator is selectively operative between ratchet and return positions.

17. The surgical instrument of claim 16, wherein:
the local anesthetic delivery actuator is pivotally disposed on said handle portion.

18. The surgical instrument of claim 16, wherein:
the handle portion further includes a pressurization mechanism disposed therein having a plunger partially disposed within said reservoir, a pair of opposed locking fingers disposed adjacent said plunger, and a ratcheting stem pivotally attached to said actuator at one end, and slidingly engaged to said plunger at an opposing end.

19. The surgical instrument of claim 16, wherein:
the incising tube is formed from a stainless steel material.

20. The surgical instrument of claim 16, wherein:
the local anesthetic inlet tube is formed from a stainless steel material.

21. The surgical instrument of claim 16, wherein:
the handle portion further includes a pressurization mechanism disposed therein having a plunger partially disposed within said reservoir.

22. The surgical instrument of claim 16, wherein:
the handle portion further includes a pair of opposed locking fingers disposed adjacent a plunger partially disposed within said reservoir.

23. The surgical instrument of claim 16, wherein:
the handle portion further includes a ratcheting stem pivotally attached to said actuator at one end and slidingly engaged to a plunger at an opposing end, the plunger partially disposed within said reservoir.

24. A surgical instrument, comprising: a
handle portion having a distal end, a proximal end, and a substantially hollow body defining a reservoir therein;

a longitudinally curved incising tube partially housed within the handle portion adjacent the handle portion distal end, extending a predetermined distance from said handle portion terminating at an incising tip, and in fluid communication with said reservoir;

a pressurization mechanism disposed in said handle portion and having a plunger partially disposed within said reservoir, a valve cap that provides pressure release without fluid release from said reservoir, said valve cap in fluid communication with said reservoir; and a local anesthetic delivery actuator disposed on said handle portion;

wherein:

said local anesthetic delivery actuator is selectively operative between ratchet and return positions to repetitively ratchetingly operate said pressurization mechanism and to selectively deliver local anesthetic through said incising tube, out said incising tip, and into a patient; and said surgical instrument is configured to be operated single-handed and without an external pressurization system.

25. The surgical instrument of claim 24, wherein:

the handle portion comprises a measured dosing window configured to allow an operator of said surgical instrument to measure how much local anesthesia has been delivered to the patient.

26. The surgical instrument of claim 24, wherein:

the handle portion comprises a local anesthesia inlet tube configured to be sealed via the valve cap and to be in fluid communication with said reservoir.

* * * * *